United States Patent
Honda

(10) Patent No.: US 12,407,919 B2
(45) Date of Patent: Sep. 2, 2025

(54) OPHTHALMOLOGY INFORMATION PROCESSING METHOD, CONTROL METHOD, AND OPHTHALMOLOGY INFORMATION PROCESSING SYSTEM

(71) Applicant: NIDEK CO., LTD., Gamagori (JP)

(72) Inventor: Naoto Honda, Gamagori (JP)

(73) Assignee: NIDEK CO., LTD.

( * ) Notice: Subject to any disclaimer, the term of this patent is extended or adjusted under 35 U.S.C. 154(b) by 29 days.

(21) Appl. No.: 18/593,472

(22) Filed: Mar. 1, 2024

(65) Prior Publication Data

US 2024/0251158 A1  Jul. 25, 2024

Related U.S. Application Data

(63) Continuation of application No. PCT/JP2021/032474, filed on Sep. 3, 2021.

(51) Int. Cl.
  *H04N 23/00* (2023.01)
  *A61B 3/12* (2006.01)
  (Continued)

(52) U.S. Cl.
  CPC .............. *H04N 23/64* (2023.01); *A61B 3/12* (2013.01); *A61B 3/14* (2013.01); *G06T 7/0012* (2013.01);
  (Continued)

(58) Field of Classification Search
  CPC ...... H04N 23/64; H04N 23/611; H04N 23/66; H04N 23/667; A61B 3/12; A61B 3/14;
  (Continued)

(56) References Cited

U.S. PATENT DOCUMENTS 7,884,977 B2 * 2/2011 Mori ............... H04N 19/12
  358/538
8,086,044 B2 * 12/2011 Feng ............... H04N 19/176
  382/220

(Continued)

FOREIGN PATENT DOCUMENTS

JP  2016-503537 A  2/2016
JP  2016-73409 A  5/2016
(Continued)

OTHER PUBLICATIONS

International Search Report mailed Nov. 16, 2021, in PCT Application No. PCT/JP2021/032474, 3 pgs.

(Continued)

*Primary Examiner* — Frank F Huang
(74) *Attorney, Agent, or Firm* — Best Mode IP Law, PLLC; Yusuke Hirai

(57) ABSTRACT

A control method includes: an instruction step of transmitting an instruction to an ophthalmological imaging device to execute an imaging-related operation; an acquisition step of acquiring, from the ophthalmology imaging device, a subject's eye image taken in accordance with the instruction; and a diagnosis support step of outputting diagnosis support information for the subject's eye image. The instruction step further includes generating the instruction to meet a specification of an API (Application Programming Interface) or an SDK (Software Development Kit) as a software interface.

6 Claims, 10 Drawing Sheets

(51) Int. Cl.
  *A61B 3/14* (2006.01)
  *G06T 7/00* (2017.01)
  *G16H 50/20* (2018.01)
  *H04N 23/60* (2023.01)
  *H04N 23/611* (2023.01)
  *H04N 23/66* (2023.01)
  *H04N 23/667* (2023.01)

(52) U.S. Cl.
  CPC ........... *G16H 50/20* (2018.01); *H04N 23/611* (2023.01); *H04N 23/66* (2023.01); *H04N 23/667* (2023.01); *G06T 2207/30041* (2013.01)

(58) Field of Classification Search
  CPC ....... A61B 3/0025; A61B 3/10; G06T 7/0012; G06T 2207/30041; G16H 50/20; G16H 30/20; G16H 30/40; G16H 40/67
  See application file for complete search history.

(56) References Cited

U.S. PATENT DOCUMENTS

| | | | | |
|---|---|---|---|---|
| 8,878,773 | B1* | 11/2014 | Bozarth | G06F 3/042 382/103 |
| 9,274,597 | B1* | 3/2016 | Karakotsios | G06F 3/0346 |
| 9,557,568 | B1* | 1/2017 | Ouderkirk | G02B 27/144 |
| 10,217,286 | B1* | 2/2019 | Angel | G06F 3/013 |
| 10,466,484 | B1* | 11/2019 | Yoon | H04N 13/332 |
| 10,466,779 | B1* | 11/2019 | Liu | G02B 27/0093 |
| 10,502,963 | B1* | 12/2019 | Noble | B29D 11/0073 |
| 2008/0143820 | A1* | 6/2008 | Peterson | G06T 7/97 348/E7.001 |
| 2008/0212942 | A1* | 9/2008 | Gordon | H04N 21/2365 348/E7.071 |
| 2009/0196460 | A1* | 8/2009 | Jakobs | G06V 40/19 382/103 |
| 2011/0234750 | A1* | 9/2011 | Lai | G03B 37/04 348/E7.001 |
| 2012/0249957 | A1* | 10/2012 | Shibata | A61B 3/0025 351/206 |
| 2012/0250980 | A1* | 10/2012 | Gillard | H04N 19/46 382/173 |
| 2012/0254369 | A1* | 10/2012 | Gillard | H04N 21/4622 709/219 |
| 2012/0257005 | A1* | 10/2012 | Browne | G02B 27/017 348/E7.001 |
| 2013/0182066 | A1* | 7/2013 | Ishimoto | E02F 9/261 348/38 |
| 2014/0037213 | A1* | 2/2014 | Niederberger | G06T 11/00 382/195 |
| 2014/0049452 | A1* | 2/2014 | Maltz | G02B 27/017 345/8 |
| 2016/0029883 | A1* | 2/2016 | Cox | G06V 40/19 351/209 |
| 2016/0085300 | A1* | 3/2016 | Robbins | H04N 23/673 345/633 |
| 2016/0241892 | A1* | 8/2016 | Cole | G06T 17/20 |
| 2016/0280136 | A1* | 9/2016 | Besson | B60R 1/31 |
| 2016/0342205 | A1* | 11/2016 | Shigeta | G06V 40/197 |
| 2018/0046859 | A1* | 2/2018 | Jarvenpaa | A61B 3/113 |
| 2018/0275409 | A1* | 9/2018 | Gao | G02B 27/0172 |
| 2018/0307048 | A1* | 10/2018 | Alexander | G03H 1/26 |
| 2019/0086674 | A1* | 3/2019 | Sinay | G06T 19/006 |
| 2020/0183174 | A1* | 6/2020 | Noui | G06F 3/013 |
| 2020/0368616 | A1* | 11/2020 | Delamont | H04N 13/239 |
| 2021/0011284 | A1* | 1/2021 | Andreev | G02B 27/0179 |
| 2021/0041948 | A1* | 2/2021 | Berkner-Cieslicki | G06F 3/011 |

FOREIGN PATENT DOCUMENTS

| | | |
|---|---|---|
| JP | 2016-073409 A | 5/2016 |
| JP | WO2019/142910 A1 | 7/2019 |
| JP | 2019-528113 A | 10/2019 |
| JP | 2020-141828 A | 9/2020 |
| JP | 2021-53457 A | 4/2021 |

OTHER PUBLICATIONS

Written Opinion mailed Nov. 16, 2021, in PCT Application No. PCT/JP2021/032474, 4 pgs. Nidek Co., Ltd.

* cited by examiner

FIG. 5

| PATIENT ID | NAME | AGE | GENDER | PAST MEDICAL HISTORY | ... | LAST EXAMINATION DATA | VISIT HISTORY |
|---|---|---|---|---|---|---|---|
| 0001 | XXXX | 64 | MALE | DIABETES | ... | 01/25/2021 | 01/25/2021 |
| | | | | | | | 06/21/2021 |
| 0002 | PATIENT B | 45 | FEMALE | REFRACTIVE SURGERY | ... | XX/XX/20XX | XX/XX/20XX |
| 0003 | PATIENT C | 71 | MALE | DIABETES / HIGH BLOOD PRESSURE | ... | XX/XX/20XX | XX/XX/20XX |
| 0004 | PATIENT D | 35 | MALE | TRAUMATIC CATARACT | ... | XX/XX/20XX | XX/XX/20XX |
| 0005 | PATIENT E | 47 | FEMALE | DRY EYE | ... | XX/XX/20XX | XX/XX/20XX |
| ⋮ | ⋮ | ⋮ | ⋮ | ⋮ | ⋮ | ⋮ | ⋮ |

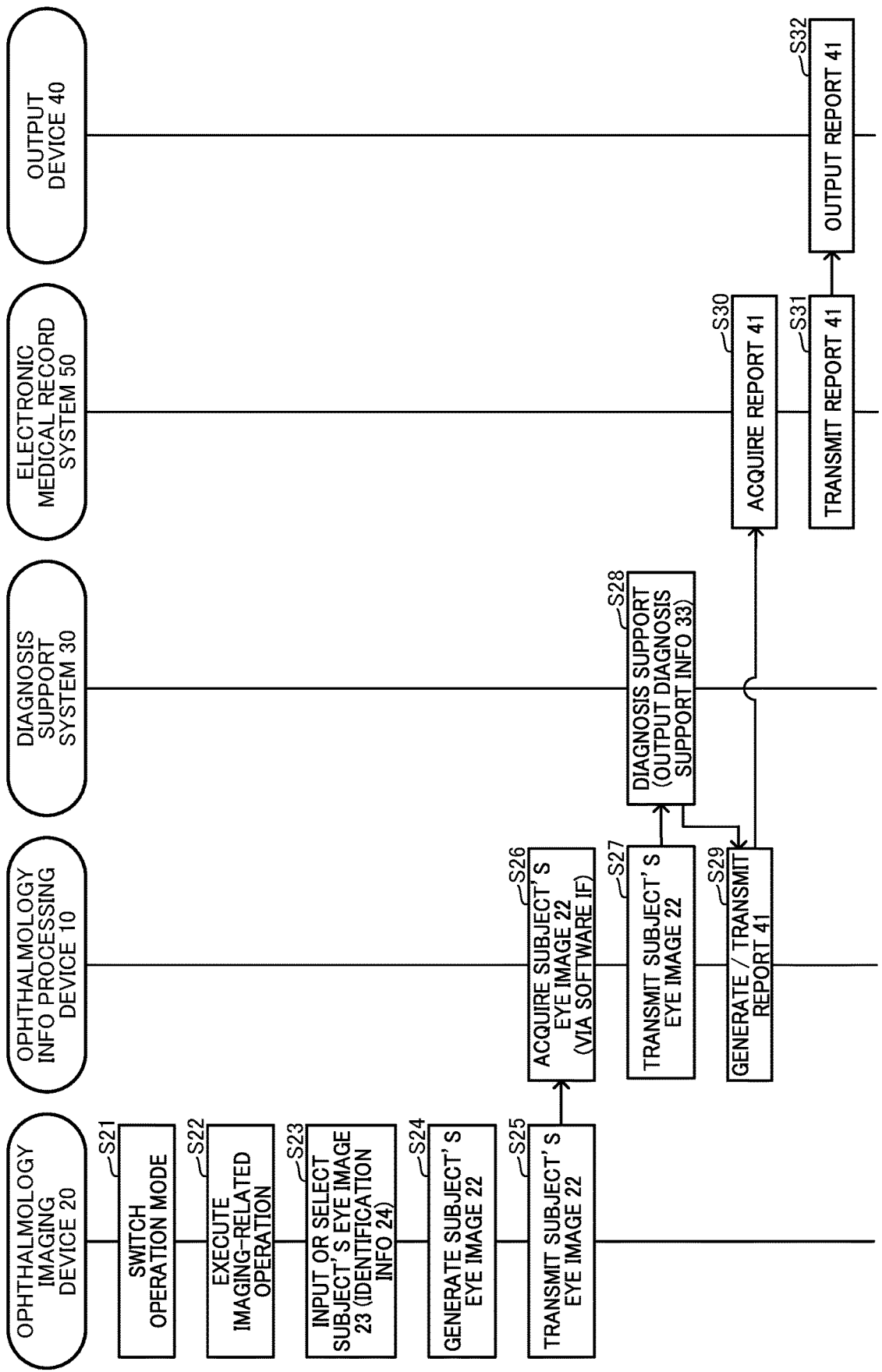

OPHTHALMOLOGY INFORMATION PROCESSING METHOD, CONTROL METHOD, AND OPHTHALMOLOGY INFORMATION PROCESSING SYSTEM

CROSS REFERENCE TO RELATED APPLICATION

This application is a continuation application of International Patent Application No. PCT/JP2021/032474 filed on Sep. 3, 2021, the entire disclosure of which is incorporated herein by reference.

TECHNICAL FIELD

The present disclosure relates to an ophthalmology information processing method, a control method, and an ophthalmology information processing system

BACKGROUND

In recent years, systemization in the ophthalmology field has progressed rapidly. In such a field, a terminal device that operates a plurality of ophthalmology devices. Further, there has been known a technique for obtaining an automatic diagnosis result for each of a plurality of diseases in the subject's eye by inputting ophthalmology images into a mathematical model trained by a machine learning algorithm.

SUMMARY

In one aspect of the present disclosure, an ophthalmology information processing method includes: generating, with an ophthalmology information processing system, an instruction for causing an ophthalmology imaging device configured to take a subject's eye image to execute an imaging-related operation including at least one of starting of an imaging sequence, stopping of the imaging sequence, switching between a left subject's eye and a right subject's eye, optimization of an imaging unit of the ophthalmology imaging device, alignment, capture, an initial operation associated with switching of patients, and transition to an imaging standby state; transmitting, with the ophthalmology information processing system, the generated instruction to the ophthalmology imaging device; taking, with the ophthalmology imaging device, the subject's eye image in accordance with the transmitted instruction; receiving, with the ophthalmology information processing system, the subject's eye image that was taken by the ophthalmology imaging device; and outputting, with the ophthalmology information processing system, diagnosis support information for the subject's eye image. Generating the instruction further comprises generating the instruction to meet a specification of an API (Application Programming Interface) or an SDK (Software Development Kit) as a software interface.

BRIEF DESCRIPTION OF DRAWINGS

FIG. 5 is a diagram showing an example of a data structure of a patient information database.

FIG. 10 is a sequence diagram showing an example of a flow of processing until a report is obtained based on a subject's eye image taken by the ophthalmology imaging device operating in a local mode.

DESCRIPTION OF EMBODIMENTS

Figure 1:
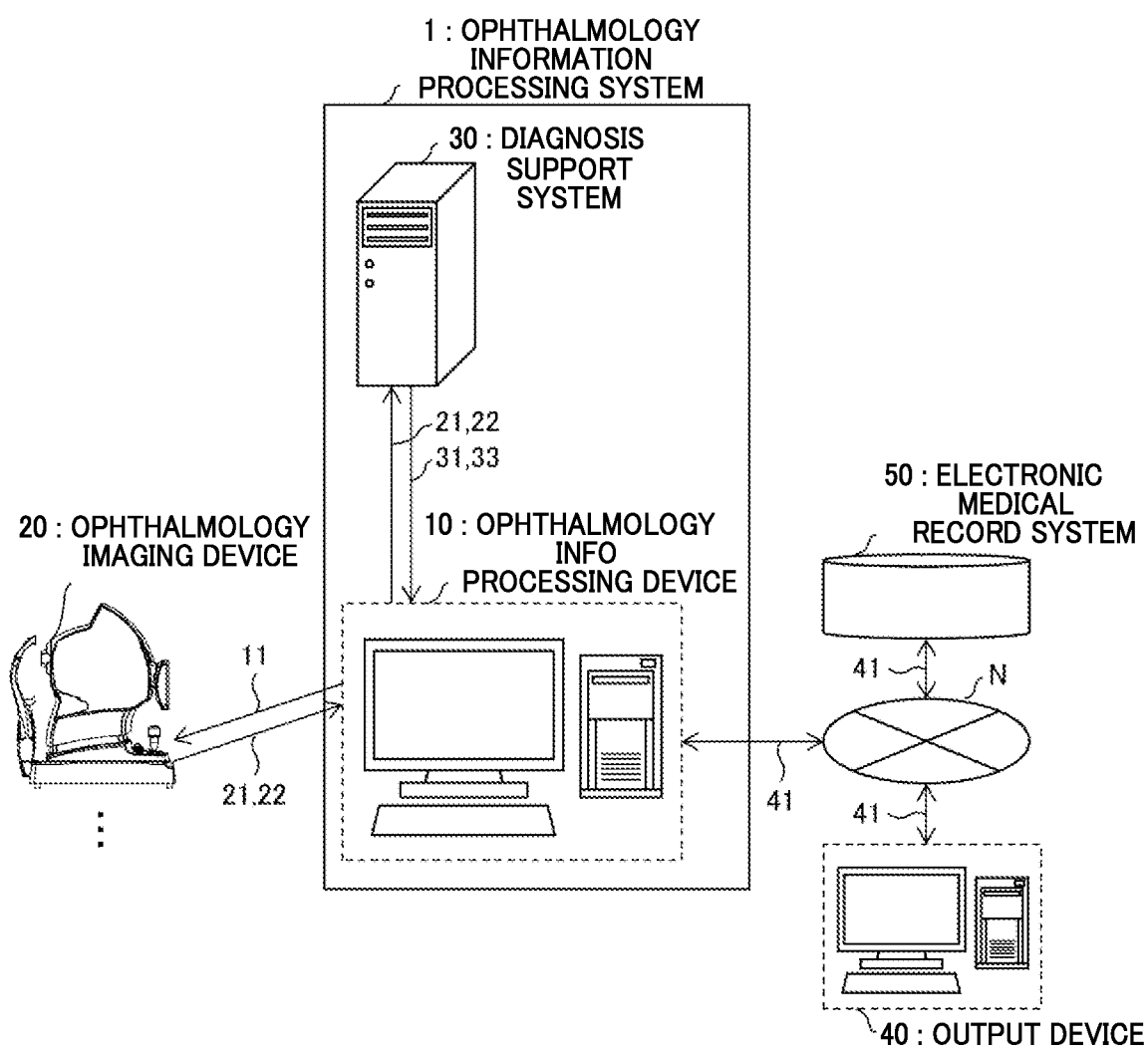
FIG. 1 is a schematic diagram showing a configuration example of an ophthalmology information processing system and peripheral devices thereof.

Next, a relevant technology will be described first only for understanding the following embodiment. Medical personnel in ophthalmology and the like felt troublesome when using the ophthalmology imaging device and the image diagnostic device. For example, dedicated software customized for each of these devices had to be used. Furthermore, data registration work had to be done separately for each of these devices. Furthermore, when introducing a new image diagnostic device, a new ophthalmology imaging device adjusted to the specifications of the newly introduced image diagnostic device had to be introduced. This led to increases in human, time, and financial costs at ophthalmology related facilities.

One aspect of the present disclosure aims to provide an ophthalmology information processing method, an ophthalmology information processing system, and a control method that are able to seamlessly perform operations from capturing an image of a subject's eye to supporting diagnosis based on the image of the subject's eye.

According to a first aspect of the present disclosure, an ophthalmology information processing method includes: generating, with an ophthalmology information processing system, an instruction for causing an ophthalmology imaging device configured to take a subject's eye image to execute an imaging-related operation including at least one of starting of an imaging sequence, stopping of the imaging sequence, switching between a left subject's eye and a right subject's eye, optimization of an imaging unit of the ophthalmology imaging device, alignment, capture, an initial operation associated with switching of patients, and transition to an imaging standby state; transmitting, with the ophthalmology information processing system, the generated instruction to the ophthalmology imaging device; taking, with the ophthalmology imaging device, the subject's eye image in accordance with the transmitted instruction; receiving, with the ophthalmology information processing system, the subject's eye image that was taken by the ophthalmology imaging device; and outputting, with the ophthalmology information processing system, diagnosis support information for the subject's eye image. Generating the instruction further comprises generating the instruction to meet a specification of an API (Application Programming Interface) or an SDK (Software Development Kit) as a software interface.

According to a second aspect of the present disclosure, a control method executed by an information processing device communicably connected to an ophthalmology imaging device including (i) an imaging unit that is configured to take a subject's eye image and (ii) an operation control unit that is configured to execute an imaging-related operation related to taking of the subject's eye image in accordance with an input operation directly input into the ophthalmology imaging device and is configured to execute the imaging-related operation in accordance with an instruction remotely transmitted. The method includes: an instruction step of transmitting the instruction to the ophthalmological imaging device as an operation target to execute the imaging-related operation; an acquisition step of acquiring, from the ophthalmology imaging device, the subject's eye image that was taken in accordance with the instruction; and a diagnosis support step of outputting diagnosis support information for the subject's eye image. The imaging-related operation includes at least one of starting of an imaging sequence, stopping of the imaging sequence, switching between a left subject's eye and a right subject's eye, optimization of the imaging unit, alignment, capture, an initial operation associated with switching of patients, and transition to an imaging standby state. The instruction step further comprises generating the instruction to meet a specification of an API (Application Programming Interface) or an SDK (Software Development Kit) as a software interface.

According to a third aspect of the present disclosure, an ophthalmology information processing system communicably connected to an ophthalmology imaging device including (i) an imaging unit that is configured to take a subject's eye image and (ii) an operation control unit that is configured to execute an imaging-related operation related to taking of the subject's eye image in accordance with an input operation directly input into the ophthalmology imaging device and is configured to execute the imaging-related operation in accordance with an instruction remotely transmitted. The system includes: at least one of (i) a circuit and (ii) a processor having a memory storing computer program code. The at least one of the circuit and the processor is configured to cause the ophthalmology information processing system to: transmit the instruction to the ophthalmological imaging device as an operation target to execute the imaging-related operation; acquire, from the ophthalmology imaging device, the subject's eye image that was taken in accordance with the instruction; and output diagnosis support information for the subject's eye image. The imaging-related operation includes at least one of starting of an imaging sequence, stopping of the imaging sequence, switching between a left subject's eye and a right subject's eye, optimization of the imaging unit, alignment, capture, an initial operation associated with switching of patients, and transition to an imaging standby state. The at least one of the circuit and the processor is further configured to cause the ophthalmology information processing system to generate the instruction to meet a specification of an API (Application Programming Interface) or an SDK (Software Development Kit) as a software interface.

According to the present disclosure, it is possible to provide an ophthalmology information processing system, an ophthalmology imaging device, and a control method that are able to seamlessly perform operations from capturing an image of a subject's eye to supporting diagnosis based on the image of the subject's eye.

Embodiment

Hereinafter, one embodiment of the present disclosure will be described in detail. FIG. 1 is a schematic diagram showing an example of the configuration of an ophthalmology information processing system 1 and its peripheral devices according to the present embodiment.

<Overview of the Ophthalmology Information Processing System 1>

The ophthalmology information processing system 1 is a system for obtaining diagnosis support information 31 and 33 based on a subject's eye image 21 captured by an ophthalmology imaging device 20. It is assumed that a business provider that designs, develops, or provides the ophthalmology imaging device 20 (hereinafter, referred to as an "ophthalmology imaging device business provider" or a "first business provider"), and a business provider that designs, develops, or provides the ophthalmology information processing system 1 (hereinafter, referred to as an "ophthalmology information processing system business provider" or a "second business provider") are different from each other.

The ophthalmology imaging device 20 includes an imaging unit (i.e., a camera) that captures an eye image 21 of a subject. The ophthalmology imaging device 20 has a function of executing an operation related to capturing the subject's eye image 21 (hereinafter, referred to as an "imaging-related operation"). A typical example of the imaging-related operation includes at least one of starting an imaging sequence, stopping the imaging sequence, switching between the left eye and the right eye, optimizing the imaging unit, alignment (adjusting the position of the device with respect to the subject's eye), capture, transfer of imaging data, initial operation associated with switching of patients, and transition to an imaging standby state. However, the imaging-related operation is not necessarily limited to the above-described examples. Optimization of the imaging unit may be, for example, focus adjustment, sensitivity adjustment, and the like. By adjusting the sensitivity, any one of light amount, gain, and exposure time can be adjusted. Further, the transition to the imaging standby state may be, for example, an operation such as switching an operation mode of the ophthalmology imaging device 20 to a power saving mode when there is no next patient after the imaging was completed.

The ophthalmology imaging device 20 may have a so-called automatic alignment function. In this case, the ophthalmology imaging device 20 may further include an alignment detection unit (not shown) and a drive unit (not shown). As an example, the alignment detection unit may detect the positional relationship between the subject's eye and the imaging unit as an alignment state. Further, the drive unit may drive the imaging unit in the XYZ directions with respect to the subject's eye. The drive section is controlled based on the detection result of the alignment state. As a result, the subject's eye and the imaging unit are adjusted to have a predetermined positional relationship suitable for imaging. Furthermore, the ophthalmology imaging device 20 may automatically capture images of the subject's eye after the automatic alignment was completed. An imaging sequence including such as an automatic alignment and an automatic imaging may be executed in one or both of a local mode and a remote mode, which will be described later.

The type of the subject's eye image 21 is not necessarily restricted as long as the image 21 is an image showing a part or all of the subject's eye. The subject's eye image 21 may be, for example, a fundus image, an anterior segment image, a corneal endothelial cell image, an angle image, or the like. That is, the ophthalmology imaging device 20 may be, for example, a fundus camera, an optical coherence tomography (OCT), and a scanning fundus imaging device (SLO: Scanning Light Ophthalmoscope), an anterior segment image analysis device, a corneal endothelial cell imaging device, a goniometric imaging device, an automatic slit lamp imaging device, or the like. Furthermore, the type of the subject's eye image based on the imaging method is not restricted. The subject's eye image may be, for example, an SLO image, a two-dimensional OCT image, a three-dimensional OCT image, a Topo image, a slit lamp image, or the like.

The ophthalmology imaging device 20 has at least an operation mode (hereinafter, referred to as a "remote mode") in which the imaging-related operation is performed in accordance with instructions from an external device (typically, the ophthalmology information processing system 1). When the ophthalmology imaging device 20 is in the remote mode, there is no need for an operator to be present near the ophthalmology imaging device 20. In the remote mode, the ophthalmology imaging device 20 does not need to request input of subject information including subject's identification information 24. In the remote mode, the ophthalmology imaging device 20 transmits the captured eye image 21 to an external device (typically, the ophthalmology information processing system 1).

In addition to the remote mode, the ophthalmology imaging device 20 has an operation mode (hereinafter, referred to as a "local mode") in which the imaging-related operation is performed according to an operation input into the device itself without being remotely controlled (that is, standalone). The ophthalmology imaging device 20 requests an input of subject information including the identification information 24 during the local mode. During the local mode, the ophthalmology imaging device 20 mayor may not transmit the subject's eye image 22 to an external device (typically, the ophthalmology information processing system 1). The subject's eye image 22 is an image in which the subject's eye image 21 and the subject's identification information 24 are associated with each other.

In the following, it is assumed that the ophthalmology imaging device 20 has the remote mode and the local mode. The ophthalmology imaging device 20 will be described as being capable of switching between the remote mode and the local mode. In other words, the ophthalmology imaging device 20 can perform the imaging-related operation in accordance with operations input into the device. Furthermore, it is assumed that the ophthalmology imaging device 20 is capable of performing the imaging-related operation in accordance with instructions from an external device. Note that if the ophthalmology imaging device 20 having the both modes is manufactured, there is no need to provide separated product lineups for the ophthalmology imaging device 20.

The ophthalmology information processing system 1 includes at least the ophthalmology information processing device 10 and a diagnosis support system 30, as shown in FIG. 1. The business provider that designs, develops, or provides the ophthalmology information processing device 10 and the business provider that designs, develops, or provides the diagnosis support system 30 may be the same or different. In other words, the ophthalmology information processing system provider may be a plurality of providers. Moreover, each function of the ophthalmology information processing device 10 and the diagnosis support system 30 may be integrated and implemented in a single information processing device. Alternatively, each function of the ophthalmology information processing device 10 and the diagnosis support system 30 may be distributed and implemented in two or more information processing devices. For example, the ophthalmology information processing device 10 may also have the functions of the diagnosis support system 30. Further, for example, the functions of the diagnosis support system 30 may be distributed to a plurality of medical facilities.

The ophthalmology information processing device 10 is communicatively connected to one or more ophthalmology imaging devices 20. The ophthalmology information processing device 10 gives instructions to each of the ophthalmology imaging devices 20 that is operating in the remote mode. Specifically, the ophthalmology information processing device 10 instructs each of the ophthalmology imaging devices 20 that is operating in the remote mode to perform the imaging-related operation. Then, the ophthalmology information processing device 10 acquires the subject's eye image 21 captured by the instructed ophthalmology imaging device 20 therefrom. At this time, one of the characteristics of the ophthalmology information processing system 1 is that a dedicated software interface provided by an ophthalmology imaging device provider is used for communication with the ophthalmology imaging device 20. The form of the software interface is not restricted. The software interface may typically be an API (Application Programming Interface) or equivalent commands. Further, the software interface may be provided as an SDK (Software Development Kit) including an API or equivalent commands. By using the dedicated software interface, the design and development of software required for interacting with the ophthalmology imaging device 20 can be easily realized at low cost. Furthermore, by using the dedicated software interface, it is useful in that the design and development of software can be realized with a high degree of freedom without subject to restrictions such as a specification of the ophthalmology imaging device 20. For example, the ophthalmology information processing system provider can directly control the ophthalmology imaging device 20. By doing so, the degree of freedom in realizing the optimization design of the entire operation including the ophthalmology information processing system 1 and in the design and development of the operation interface, etc. can be increased. It is even more useful when working with a plurality of ophthalmology imaging devices 20 having different specifications. It should be noted that conventional control software used to control an ophthalmology imaging device was usually only installed and used, and was not able to be flexibly improved. In other words, it was difficult to perform design and development with a high degree of freedom as described above.

The ophthalmology information processing device 10 transmits the subject's eye images 21 and 22 acquired from the ophthalmology imaging device 20 to the diagnosis support system 30 that is communicably connected the processing device 10. The diagnosis support system 30 is a system for providing diagnosis support. The diagnosis support system 30 receives the image of the subject's eye 21, as input, acquired from the ophthalmology information processing device 10. The diagnosis support system 30 then outputs diagnosis support information 31 for the subject's eye image 21. Furthermore, the diagnosis support system 30 receives the subject's eye image 22 acquired from the ophthalmology information processing device 10 as input. The diagnosis support system 30 then outputs diagnosis support information 33 for the subject's eye image 22. Typically, one or more computers in the diagnosis support system 30 performs the diagnosis support. However, one or more doctors may perform the diagnosis support. The process on the subject's eye images 21 and 22 is not restricted. For example, such a process may include analysis processing, processing using artificial intelligence, or a combination thereof.

The diagnosis support system 30 transmits the output diagnosis support information 31 and 33 to the ophthalmology information processing device 10.

The ophthalmology information processing device 10 may generate diagnosis support information 32. The diagnosis support information 32 is associated with (i) the diagnosis support information 31 acquired from the diagnosis support system 30 and (ii) the identification information 54 of a subject whose subject's eye image, which is the source of the diagnosis support information 31, was taken. Here, the source of the identification information 54 is not necessarily the ophthalmology imaging device 20. That is, one of the features of the ophthalmology information processing system 1 is that the diagnosis support information 32 associated with the identification information 54 can be generated without depending on the ophthalmology imaging device 20. Accordingly, it is not necessary to register and manage identification information of the subject at the ophthalmology imaging device 20. Furthermore, the identification information does not need to be linked between the ophthalmology imaging device 20 and the ophthalmology information processing system 1. Therefore, it is possible to reduce the complexity associated with registering and managing the identification information of the subject. Note that conventionally the identification information of a subject had to be registered at the ophthalmology imaging device. Furthermore, even in a system that handled images of the subject's eye taken by an ophthalmology imaging device, the identification information of the subject was usually registered for the system, which made data registration and data management complicated.

The source of the identification information 54 is, for example, but not limited to, an electronic medical record system 50 communicatively connected to the ophthalmology information processing device 10. The electronic medical record system 50 is a system having a database that manages electronic medical records including patient information. Note that the managing operation manner in the electronic medical record system 50 may be different from that of the ophthalmology information processing system 1.

The ophthalmology information processing device 10 may generate a report 41 including the diagnosis support information 32 or the diagnosis support information 33. The report 41 may include the images 21 and 22 of the subject's eye. The ophthalmology information processing device 10 may transmit the generated report 41 to the electronic medical record system 50 via a communication network N. The report 41 may be stored in the electronic medical record system 50. The report 41 may be transmitted to an output device 40 directly from the electronic medical record system 50 or via the ophthalmology information processing system 1. Typical examples of the output device 40 are a PC (Personal Computer) used by a medical professional or a patient, an information processing terminal device such as a tablet terminal device, a printer, etc. However, other devices may serve as the output device 40 as long as the devices are capable of displaying, printing, or the like, the report 41.

The ophthalmology information processing system 1 includes the functions as described above. Therefore, the ophthalmology information processing system 1 is a system that is functionally different from a conventional information processing terminal device equipped with control software for controlling an ophthalmology imaging device and an image viewer for viewing images of the subject's eye taken by the ophthalmology imaging device. According to the ophthalmology information processing system 1, it is possible to seamlessly perform operations from taking the subject's eye image to supporting diagnosis based on the subject's eye image. In other words, it is possible to reduce the workload of ophthalmology medical personnel.

Furthermore, as described above, the ophthalmology information processing system 1 provided by the ophthalmology information processing system provider uses the dedicated software provided by the ophthalmological imaging device provider when communicating with the ophthalmology imaging device 20 provided by the ophthalmological imaging device provider. For example, the ophthalmology information processing system 1 generates instructions in line with specifications of the software interface. Then, the ophthalmology information processing system 1 gives the instructions to the ophthalmology imaging device 20. Further, the ophthalmology imaging device 20 executes the imaging-related operations based on the instructions. Therefore, the ophthalmology information processing system 1 provided by the ophthalmology information processing system provider can perform a series of processes from taking the subject's eye image 21 by the ophthalmology imaging device 20 to obtaining the diagnosis support information 31, 33 based on the subject's eye image 21 without subject to constraints by other specifications, environment, etc. of the ophthalmology imaging device 20 provided by the ophthalmology imaging device provider. Further, for the ophthalmology imaging device provider, there is no need to customize the ophthalmology imaging device 20 to meet the specifications of the ophthalmology information processing system 1 provided by the ophthalmology information processing system provider. Therefore, the ophthalmology imaging device 20 can be operated based on instructions from the ophthalmology information processing system 1.

Example of Arrangement of Devices

Figure 2:
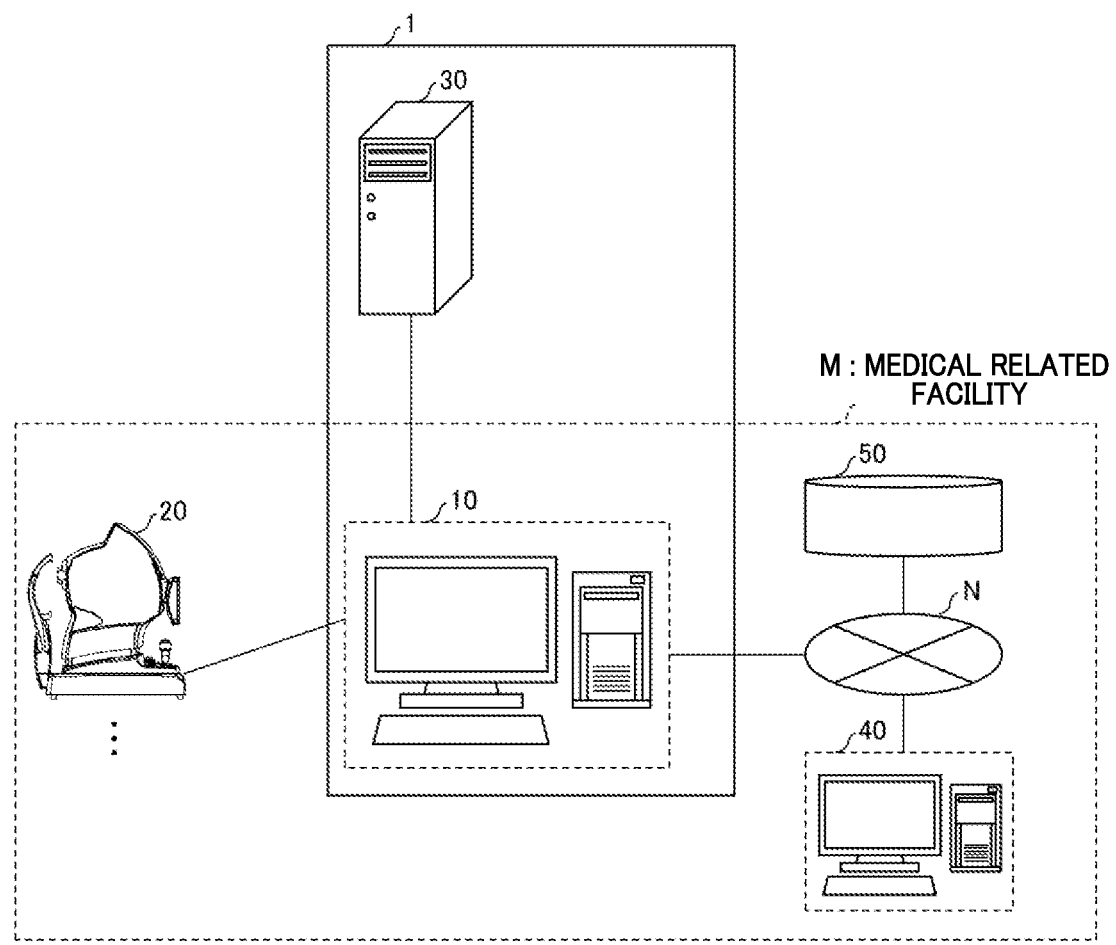
FIG. 2 is a schematic diagram showing an example of the arrangement of the ophthalmology information processing system and the peripheral devices.

One example of the arrangement of devices will be described with reference to FIGS. 2 and 3. A typical example of the location where the ophthalmology information processing device 10 is located in a medical related facility M, as shown in FIG. 2. A typical example of the medical related facility M is a hospital. However, the medical related facility M may be a clinic, a testing facility, a pharmacy, a drug store, or an ophthalmology related store. The ophthalmology information processing device 10 is connected to the communication network N including a LAN (Local Area Network) installed in, e.g., the medical related facility M.

A typical example of the location of the diagnosis support system 30 is, as shown in FIG. 2, a facility different from the medical related facility M where the ophthalmology information processing device 10 is located. In this case, the ophthalmology information processing device 10 is connected to the diagnosis support system 30 via, for example, a VPN (Virtual Private Network) on the Internet. The diagnosis support system 30 may be a system configured by a server or the like built on a cloud. Note that the diagnosis support system 30 may be placed in the medical related facility M where the ophthalmology information processing device 10 is located. In this case, the ophthalmology information processing device 10 and the diagnosis support system 30 are connected to each other via the LAN installed in the medical related facility M.

A typical example of the location for the output device 40 is the medical related facility M where the ophthalmology information processing device 10 is placed, as shown in FIG. 2. In this case, the output device 40 is connected to the communication network N including the LAN installed in the medical related facility M, for example. Alternatively, the output device 40 may be placed in a facility different from the medical related facility M where the ophthalmology information processing device 10 is placed. In this case, the communication network N to which the output device 40 is connected may include a VPN on the Internet or the like. Furthermore, the output device 40 may be a portable device and may not be fixedly placed.

A typical example of the location for the electronic medical record system 50 is the medical related facility M where the ophthalmology information processing device 10 is located. In this case, the electronic medical record system 50 is connected to the communication network N including the LAN installed in the medical related facility M, for example.

The ophthalmology imaging device 20 may be located in a variety of locations. A first typical example of the location for the ophthalmology imaging device 20 is the medical related facility M, as shown in FIG. 2 The ophthalmology imaging device 20 located in the medical related facility M is connected to the ophthalmology information processing device 10 via the LAN installed in the medical related facility M. A plurality of ophthalmology information processing devices 10 may be placed in the medical related facility M. In the case of the example shown in FIG. 2, the subject's eye images 21 and 22 are taken, the diagnosis support information 31 and 33 are acquired, and the report 41 is output in the medical related facility M. The operators of the ophthalmology imaging device 20, the ophthalmology information processing device 10, and the output device 40 may be the same person.

Figure 3:
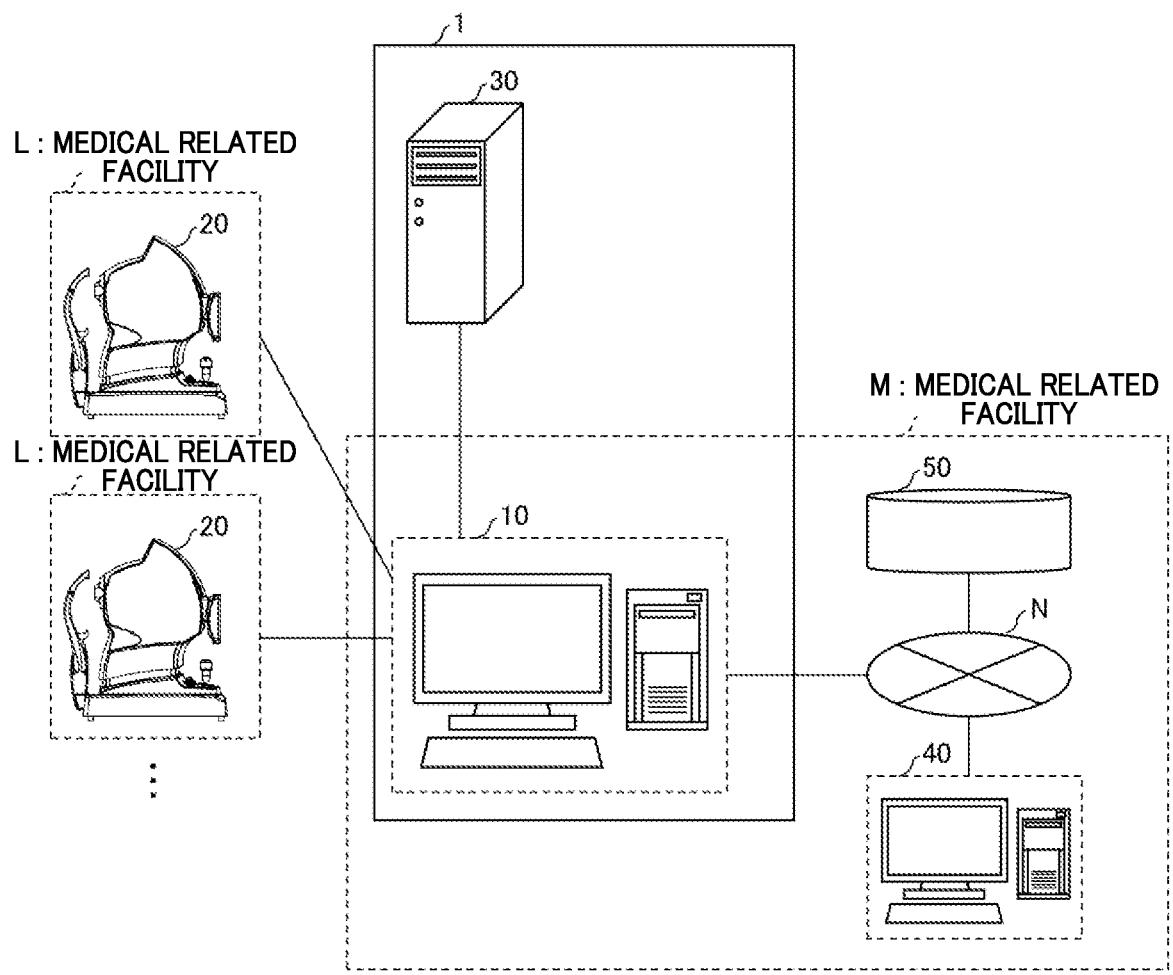
FIG. 3 is a schematic diagram showing an example of the arrangement of the ophthalmology information processing system and its peripheral devices.

A second typical example of the location for the ophthalmology imaging device 20 is a medical related facility L that is different from the medical related facility M, as shown in FIG. 3. The medical related facility L may be a clinic, a testing facility, a pharmacy, a drug store, or an ophthalmology-related store. The ophthalmology imaging device 20 located in the medical related facility L is connected to the ophthalmology information processing device 10 via, for example, a VPN on the Internet. As shown in FIG. 3, each of the plurality of ophthalmology imaging devices 20 may be placed in a mutually different one of the medical related facilities L. In the example shown in FIG. 3, each of the subject's eye images 21 and 22 taken at one or more medical related facilities L is collected at one medical related facility M. Then, the medical related facility M acquires the diagnosis support information 31 and 33 and outputs the report 41. In the case of the example shown in FIG. 3, the operator of the ophthalmology imaging device 20 and the operators of the ophthalmology information processing device 10 and the output device 40 are usually different from each other. It is assumed that the ophthalmology imaging devices 20 placed in the respective medical related facilities L may have different specifications, environments, and the like. Therefore, in the example shown in FIG. 3, it is preferable that the ophthalmology information processing system 1 utilizes a dedicated software interface when communicating with the ophthalmology imaging device 20.

<Main Configuration of the Ophthalmology Information Processing System 1>

Figure 4:
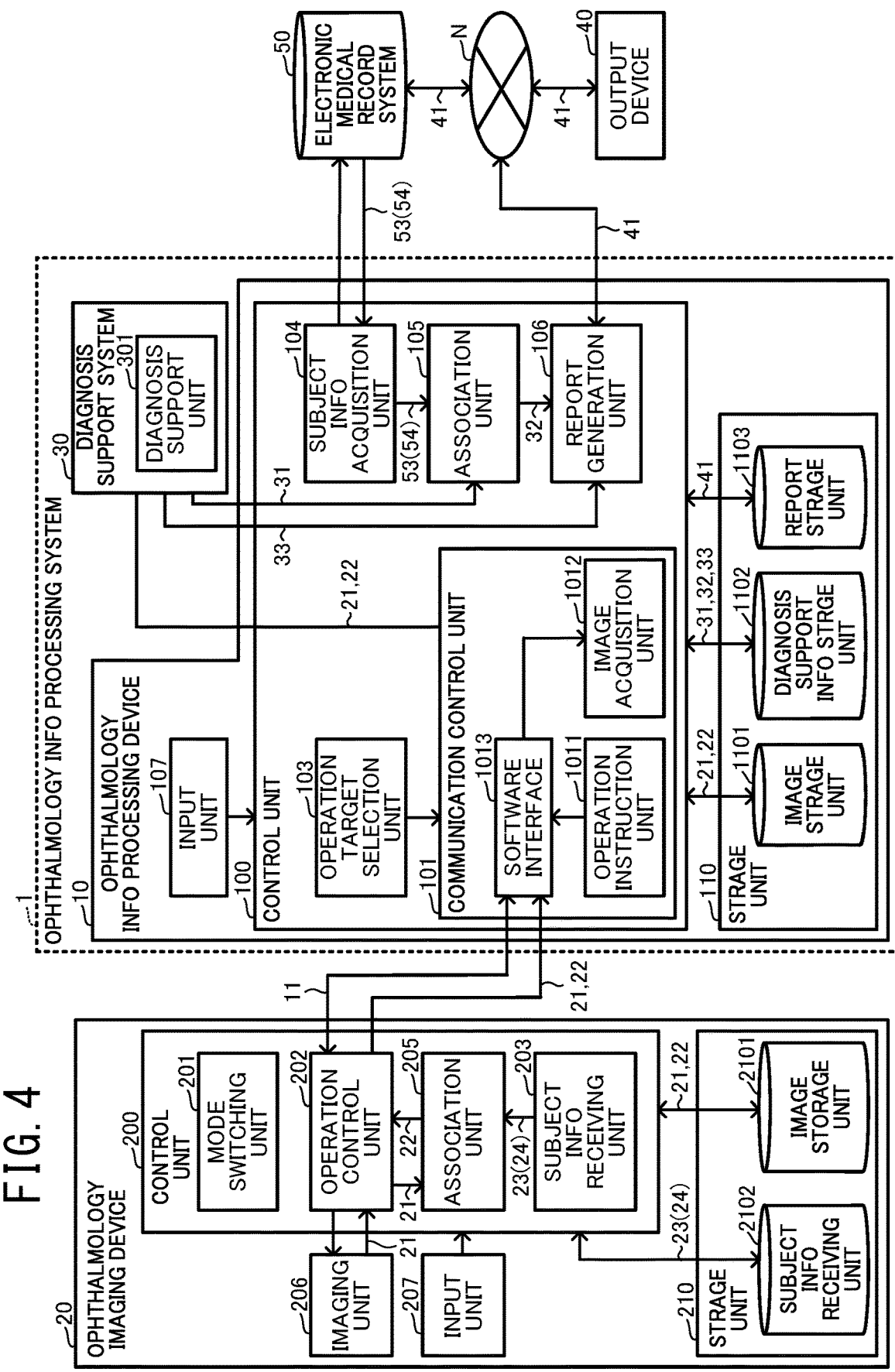
FIG. 4 is a block diagram showing the configuration of main parts of the ophthalmology information processing system and an ophthalmology imaging device.

FIG. 4 is a block diagram showing the main configuration of the ophthalmology information processing system 1 and the ophthalmology imaging device 20. As described above, the ophthalmology information processing system 1 typically includes the ophthalmology information processing device 10 and the diagnosis support system 30.

(Ophthalmology Information Processing Device 10)

The ophthalmology information processing device 10 includes an input unit 107, a control unit 100, and a storage unit 110.

The input unit 107 is a device that accepts input operations input into the ophthalmology information processing device 10. For example, the input unit 107 may be a keyboard, a mouse, a touch panel, and a microphone. When the input unit 107 is a touch panel, the input unit 107 may also have an information display function. The input unit 107 outputs a signal corresponding to the received input operation to the control unit 100.

The storage unit 110 is a memory that stores various data and various software used by the ophthalmology information processing device 10. Alternatively, the storage unit 110 may be a storage device connected to the ophthalmology information processing device 10.

The storage unit 110 may include an image storage unit 1101, a diagnosis support information storage unit 1102, and a report storage unit 1103. The image storage unit 1101 stores the subject's eye images 21 and 22. The diagnosis support information storage unit 1102 stores the diagnosis support information 31 and 33. The report storage unit 1103 stores the report 41.

The control unit 100 comprehensively controls each function of the ophthalmology information processing device 10. The control unit 100 is, for example, a processor such as a CPU (Central Processing Unit). For example, the control unit 100 reads out a program for performing each function from the storage unit 110 and sends the program in a RAM (Random Access Memory). That is, the control unit 100 includes at least a communication control unit 101. The communication control unit 101 includes an operation instruction unit 1011, an image acquisition unit 1012, and a software interface (hereinafter, referred to as "software IF") 1013. Further, the control unit 100 may include an operation target selection unit 103, a subject information acquisition unit 104, an association unit 105, and a report generation unit 106.

Programs for performing functions of the operation instruction unit 1011, the image acquisition unit 1012, the subject information acquisition unit 104, the association unit 105, and the report generation unit 106 are provided by the ophthalmology information processing system provider. On the other hand, the software IF 1013 is provided from the ophthalmology imaging device provider directly or via an intermediary provider to the ophthalmology information processing system provider.

The operation target selection unit 103 selects an ophthalmology imaging device 20, as an operation target, from among the plurality of ophthalmology imaging devices 20. The ophthalmology imaging device 20, as an operation target, is an ophthalmology imaging device that is configured to operate in a remote mode. Note that if only one predetermined ophthalmology imaging device 20 exists as an operation target, there is no need for the operation target selection unit 103 to select the ophthalmology imaging device 20. Alternatively, the operation target selection unit 103 may select the ophthalmology imaging device 20 as an operation target, in accordance with the input operation received by the input unit 107. Furthermore, the operation target selection unit 103 may automatically select the ophthalmology imaging device 20, as an operation target, based on a predetermined rule.

The operation instruction unit 1011 instructs the ophthalmology imaging device 20 to perform the imaging-related operation. It is preferable that the instructions meet the specifications of the software IF 1013 (that is, the instructions are generated via the software IF 1013). Specifically, it is preferable that the operation instruction unit 1011 transmits a command 11 that meets the specifications of the software IF 1013 to cause the ophthalmology imaging device 20 to perform the imaging-related operation.

The software IF 1013 instructs the ophthalmology imaging device 20 to perform the imaging-related operation. The software IF 1013 is an aggregation of dedicated software interfaces for acquiring the subject's eye images 21 and 22. The software IF 1013 is typically an aggregation of APIs. For example, the software IF 1013 is distributed or downloaded to the ophthalmology information processing device 10 from a server (not shown) that provides the software IF 1013. Furthermore, the software IF 1013 is installed in the ophthalmology information processing device 10. Further, as an example, the software IF 1013 stored on a storage medium such as a USB (Universal Serial Bus) memory may be read and installed in the ophthalmology information processing device 10. In this way, the method of providing the software IF 1013 is not restricted.

The timing at which the operation instruction unit 1011 instructs the ophthalmology imaging device 20 to perform the imaging-related operations is not restricted. The timing may be, for example, a timing immediately after the ophthalmology imaging device 20 was selected by the operation target selection unit 103. Alternatively, the timing may be a timing upon receiving an input operation by the input unit 107. Furthermore, the timing may be determined based on a predetermined rule.

The image acquisition unit 1012 acquires the subject's eye image 21 that was taken by the ophthalmology imaging device 20 which was operating in the remote mode according to instructions from the operation instruction unit 1011. It is preferable that the image acquisition unit 1012 acquires the subject's eye image 21 via the software IF 1013.

The image acquisition unit 1012 transmits the subject's eye image 21 acquired from the ophthalmology imaging device 20 to the diagnosis support system 30. The transmission timing of the subject's eye image 21 is not restricted. The transmission timing of the subject's eye image 21 may be, for example, a timing immediately after the image acquisition unit 1012 acquired the subject's eye image 21. Further, the transmission timing may be a timing upon receiving an input operation by the input unit 107. Furthermore, the timing may be a timing determined based on a predetermined rule.

The image acquisition unit 1012 may store the subject's eye image 21 acquired from the ophthalmology imaging device 20 in the image storage unit 1101. The storage timing of the subject's eye image 21 is not restricted. For example, the storage timing may be a timing immediately after the image acquisition unit 1012 acquired the subject's eye image 21. Alternatively, the storage timing may be a timing before the image acquisition unit 1012 transmits the subject's eye image 21 to the diagnosis support system 30. Furthermore, the storage timing may be a timing after the image acquisition unit 1012 transmitted the subject's eye image 21 to the diagnosis support system 30. Yet furthermore, the storage timing may be a timing determined based on a predetermined rule.

The image acquisition unit 1012 may acquire the subject's eye image 22 that was taken by the ophthalmology imaging device 20 which was operating in the local mode. Also in this case, the image acquisition unit 1012 preferably acquires the subject's eye image 22 via the software IF 1013. The image acquisition unit 1012 may transmit the acquired subject's eye image 22 to the diagnosis support system 30. The transmission timing of the subject's eye image 22 is not restricted. The transmission timing may be, for example, a timing immediately after the image acquisition unit 1012 acquired the subject's eye image 22. Further, the transmission timing may be a timing upon receiving an input operation by the input unit 107, or a timing determined based on a predetermined rule.

The image acquisition unit 1012 may store the acquired subject's eye image 22 in the image storage unit 1101. The storage timing of the subject's eye image 22 is not restricted. The storage timing may be various timings. For example, the subject's eye image 22 may be stored immediately after the image acquisition unit 1012 acquired the subject's eye image 22. Alternatively, the subject's eye image 22 may be stored before the image acquisition unit 1012 transmits the subject's eye image 22 to the diagnosis support system 30. Furthermore, the subject's eye image 22 may be stored after the image acquisition unit 1012 transmitted the subject's eye image 22 to the diagnosis support system 30, or the subject's eye image 22 may be stored at a timing determined based on a predetermined rule.

The subject information acquisition unit 104 acquires subject information 53 that includes at least the identification information 54 of the subject whose eye image 21 is to be taken. The subject information acquisition unit 104 may acquire the subject information 53 in response to an input operation received by the input unit 107. The acquisition timing of the subject information 53 is not restricted. The acquisition timing may be, for example, a timing before the image acquisition unit 1012 transmits the subject's eye image 21 to the diagnosis support system 30. Further, the acquisition timing may be a timing after the image acquisition unit 1012 transmitted the subject's eye image 21 to the diagnosis support system 30, or may be a timing determined according to an input operation received by the input unit 107.

The source of the subject information 53 is, for example, a patient information database 501 included in the electronic medical record system 50. The patient information database 501 is a database that stores patient information.

FIG. 5 is a diagram showing an example of a data structure of the patient information database 501. The patient information database 501 is shown in FIG. 5. The patient information database 501 may include information such as name, age, gender, medical history, previous examination date, hospital visit history, etc. as the subject information 53, using a patient ID, which is the identification information 54, as a key. Furthermore, the patient information database 501 may further include information such as past subject's eye images 21 and 22, the diagnosis support information 31 and 33, and findings. In addition to the patient ID as the identification information 54, the subject information acquisition unit 104 may acquire, from the patient information database 501, respective pieces of the above-mentioned information associated with the patient ID.

The association unit 105 acquires the diagnosis support information 31 for the subject's eye image 21 for the subject from the diagnosis support system 30. The association unit 105 generates the diagnosis support information 32 attached with the identification information. The diagnosis support information 32 is generated by associating the acquired diagnosis support information 31 with the subject information 53 (including at least the identification information 54). This subject information 53 is information about the subject whose eye image 21 was taken. The diagnosis support information 31 is originated from the subject's eye image. The information 53 is acquired by the subject information acquisition unit 104. The generation timing of the diagnosis support information 32 is not restricted. The generation timing of the diagnosis support information 32 may be, for example, a timing immediately after acquiring both the diagnosis support information 31 and the subject information 53. Alternatively, the diagnosis support information 32 may be generated upon receiving an input operation by the input unit 107.

As described above, the identification information 54 is acquired from the patient information database 501 of the electronic medical record system 50. That is, the ophthalmology information processing system 1 can generate the diagnosis support information 32 associated with the identification information 54 without depending on the ophthalmology imaging device 20. Therefore, it is not necessary to register and manage identification information of subjects in the ophthalmology imaging device 20. Furthermore, the identification information does not need to be linked between the ophthalmology imaging device 20 and the ophthalmology information processing system 1. For the reasons described above, using the ophthalmology information processing system 1, it is possible to reduce the complexity involved in registering and managing the identification information of subjects.

Figure 6:
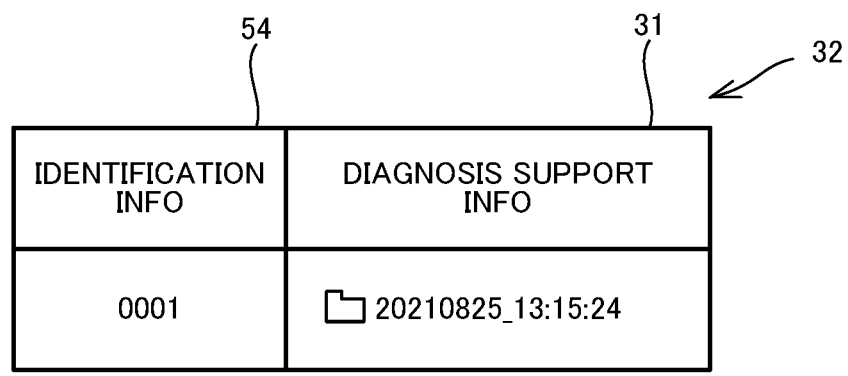
FIG. 6 is a diagram showing an example of a data structure of diagnosis support information with identification information.

FIG. 6 is a diagram showing an example of the data structure of the diagnosis support information 32 attached with the identification information. In the example shown in FIG. 6, the diagnosis support information 31 is expressed in a single folder. It should be understood that one or more files (not shown) related to the diagnosis support information 31 are presented in the folder. In the example shown in FIG. 6, only the identification information 54 is associated with the diagnosis support information 31, but the present disclosure is not necessarily limited to this. For example, in addition to the identification information 54, the association unit 105 may generate the diagnosis support information 32 by associating each piece of information acquired by the subject information acquisition unit 104 from the patient information database 501 with the diagnosis support information 31. The information acquired by the subject information acquisition unit 104 includes, for example, name, age, gender, medical history, previous examination date, hospital visit history, past subject's eye images 21 and 22, and findings.

The association unit 105 may store the diagnosis support information 31 and 32 in the diagnosis support information storage unit 1102. Alternatively, the association unit 105 may store the diagnosis support information 31 and 32 in the patient information database 501.

The report generation unit 106 generates the report 41 including the diagnosis support information 32. The report generation unit 106 may acquire the diagnosis support information 32 from the association unit 105. Alternatively, the report generation unit 106 may read the diagnosis support information 32 from the diagnosis support information storage unit 1102.

Further, the report generation unit 106 generates the report 41 including the diagnosis support information 33 for the subject's eye image 22. The report generation unit 106 may acquire the diagnosis support information 33 from the diagnosis support system 30. Alternatively, the report generation unit 106 may read the diagnosis support information 33 from the diagnosis support information storage unit 1102.

The generation timing of the report 41 is not restricted, and may be, for example, a timing immediately after the report generation unit 106 acquired the diagnosis support information 32 and 33. Alternatively, the report 41 may be generated upon receiving an input operation by the input unit 107. The report generation unit 106 may store the generated report 41 in the report storage unit 1103. The report generation unit 106 may store the acquired diagnosis support information 32 and 33 in the diagnosis support information storage unit 1102.

A reader of the report 41 may be medical personnel, a subject, or both. Therefore, the report generation unit 106 may generate the report 41 in a displaying format according to the reader. For example, the report 41 for medical personnel may highly detailed or may use ophthalmology terminology. On the other hand, the report 41 for subjects may be less detailed or may not use ophthalmology terminology. Alternatively, the report generation unit 106 may determine the display format of the report 41 according to an input operation received by the input unit 107.

The report generation unit 106 transmits the generated report 41 to the electronic medical record system 50 via the communication network N. The transmission timing of the report 41 is not limited. For example, the report generation unit 106 may transmit the report 41 at a timing immediately after generating the report 41. Further, the report 41 may be transmitted at a timing upon receiving an input operation by the input unit 107. Note that the electronic medical record system 50 may transmit the report 41 to the output device 40 directly or via the ophthalmology information processing system 1. The output device 40 as an output destination may be determined in advance. Alternatively, the output device 40 as an output destination may be determined according to an input operation received by the electronic medical record system 50. Furthermore, the output device 40 as an output destination may be determined according to an input operation received by the ophthalmology information processing system 1. The method for transmitting to the output device 40 is not restricted. For example, the report 40 may be transmitted using a file transfer system. Alternatively, the report 40 may be transmitted as an attachment to a general-purpose email. The file format of the report 41 is not limited, and may be, for example, PDF (Portable Document Format).

The report generation unit 106 may directly transmit the generated report 41 to the output device 40. Further, the report generation unit 106 may store the generated report 41 in the report storage unit 1103.

Figure 7:
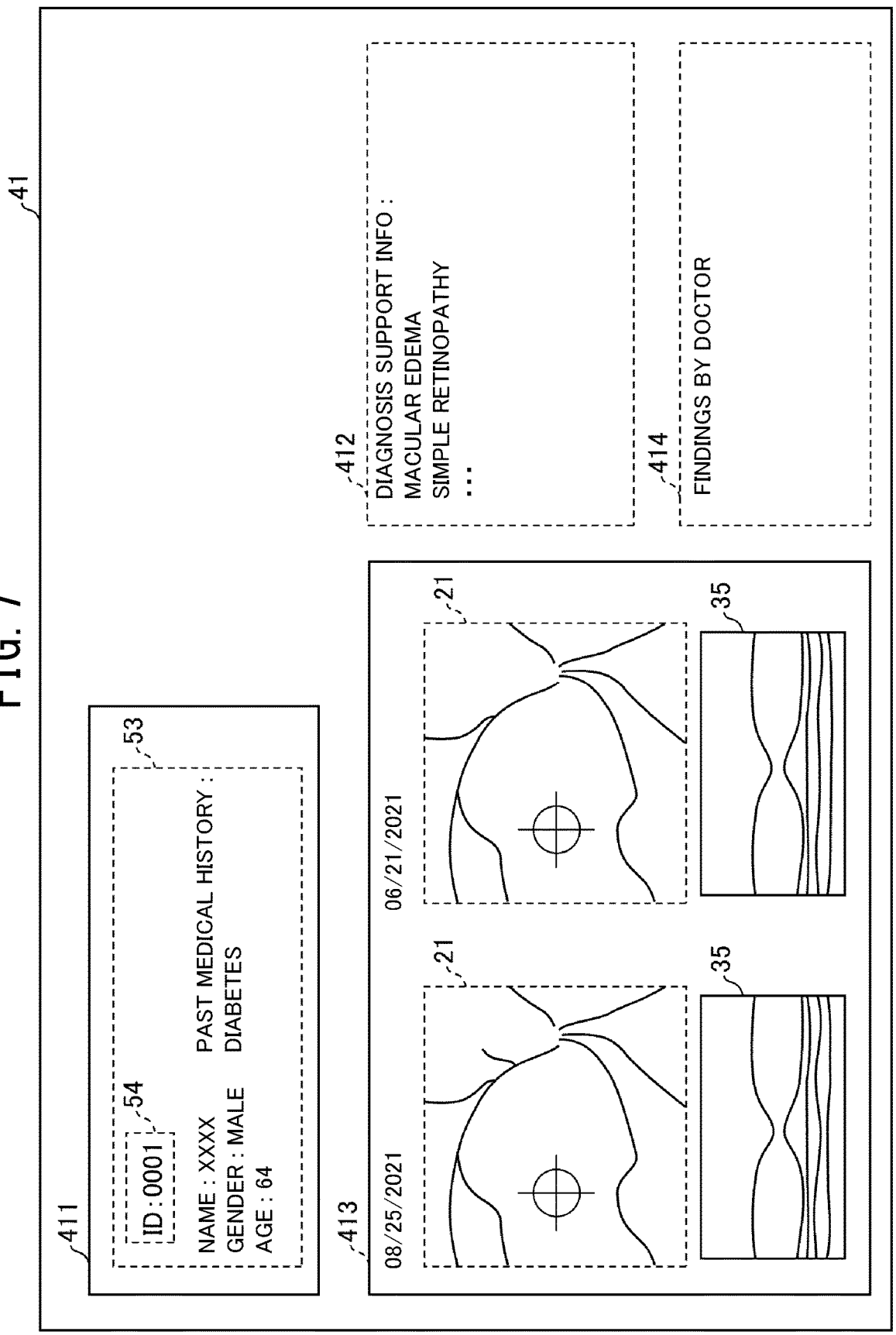
FIG. 7 is a diagram showing an example of a report.

FIG. 7 is a diagram showing an example of the report 41. The report 41 shown in FIG. 7 shows one example including the diagnosis support information 32. The report 41 includes, for example, a subject information display area 411 and a diagnosis support information display area 412. Further, the report 41 may further include, for example, an image display area 413 and a findings display area 414.

In the subject information display area 411, all or a part of the subject information 53 associated with the diagnosis support information 32 is displayed. The subject information display area 411 may display, for example, the identification information 54, name, gender, age, medical history, previous examination date, hospital visit history, and the like. For example, if the subject needs to be prevented from being identified, the name may not be displayed.

In the diagnosis support information display area 412, all or a part of the text indicating the diagnosis support information included in the diagnosis support information 32 is displayed. FIG. 7 shows one example of symptoms of diabetic retinopathy and severity classification. As an example, texts such as "macular edema" and "simple retinopathy" are displayed.

The image display area 413 displays, for example, the subject's eye image 21 (which may be processed by, e.g., highlighting an abnormal location) included in the diagnosis support information 32. Further, in the image display area 413, the image analysis result 35 of the subject's eye image 21, etc. are displayed. The image display area 413 may display, for example, a past subject's eye image 21 of the same subject and image analysis results of the subject's eye images 21. By displaying the past subject's eye images 21, medical personnel and the patient can easily check the progress of symptoms.

The findings display area 414 is, for example, an area for medical personnel to note their findings therein. The report 41 with the noted findings may be transmitted to an information processing terminal device used by the subject. At this time, the report 41 is transmitted from the information processing terminal device used by the doctor directly or via the ophthalmology information processing system 1 to the information processing terminal device of the subject.
(Diagnosis Support System 30)

The diagnosis support system 30 includes a diagnosis support unit 301. The diagnosis support unit 301 receives, as an input, the subject's eye image 21 acquired from the ophthalmology information processing device 10 and outputs, as an output, diagnosis support information 31 on the subject's eye image 21. Similarly, the diagnosis support unit 301 receives as an input, the subject's eye image 22 acquired from the ophthalmology information processing device 10 and outputs, as an output, diagnosis support information 33 on the subject's eye image 22. The processing contents by the diagnosis support unit 301 may be image analysis or processing using artificial intelligence. When using artificial intelligence, the diagnosis support unit 302 may use a diagnosis model generated by machine-learning the correlation between the subject's eye image and the diagnosis support information.

A program for realizing functions of the diagnosis support unit 301 is provided by the ophthalmology information processing system provider.

The diagnosis support information 31, 33 may be formed of one or more electronic files including images, texts, numerical data, and combinations thereof. The images included in the diagnosis support information 31 and 33 include the subject's eye images 21 and 22 themselves, and images that have been processed by, e.g., highlighting abnormalities in the subject's eye images 21 and 22. However, the images included in the diagnosis support information 31 and 33 are not necessarily limited to these. The texts included in the diagnosis support information 31 and 33 may be a text representing an image analysis result, a text representing diagnosis support information, a text representing a treatment method, and the like. However, it is not necessarily limited to these. Specific examples of the text included in the diagnosis support information 31 and 33 include disease name, symptoms, degree of progress of symptoms, and therapeutic drugs. However, it is not necessarily limited to these.

As an example, it is assumed that the subject's eye images 21 and 22 are retinal images, and macular edema is recognized through diagnosis support. In this case, the diagnosis support unit 301 may output the diagnosis support information 31 and 33 including an image clearly showing the location of macular edema and a text such as "MACULAR EDEMA PRESENT" and "SIMPLE RETINOPATHY". Accordingly, it possible to create the report 41 as shown in FIG. 7, for example.
<Main Configuration of the Ophthalmology Imaging Device 20>

Returning back to FIG. 4, the main configuration of the ophthalmology imaging device 20 will be described. The ophthalmology imaging device 20 is shown in FIG. 4. The main component of the ophthalmology imaging device 20 includes, for example, a control unit 200, an imaging unit 206, an input unit 207, and a storage unit 210.

The imaging unit 206 is a camera for taking the subject's eye image 21. The imaging unit 206 is controlled by an operation control unit 202, which will be described later. The imaging unit 206 may add EXIF (Exchangeable Image File Format) information such as imaging date and time and position information to the subject's eye image 21.

The input unit 207 is a device that accepts input operations into the ophthalmology imaging device 20. A typical example of the input operation is an operation for causing the ophthalmology imaging device 20 operating in the local mode to perform the imaging-related operation. Furthermore, a typical example of the input operation is an operation for inputting or selecting the subject information 23.

The input unit 207 may be, for example, a touch panel, a button, or a switch mounted in the ophthalmology imaging device 20. Further, the input unit 207 may be a mouse and a keyboard of an information terminal device connected to the ophthalmology imaging device 20. When the input unit 207 is a touch panel, the input unit 207 may also have an information display function. The input unit 207 outputs a signal corresponding to the received input operation to the control unit 200.

The storage unit 210 is a memory that stores various data and various software used by the ophthalmology imaging device 20. Alternatively, the storage unit 210 may be a storage device connected to the ophthalmology imaging device 20. Furthermore, the storage unit 210 may include an image storage unit 2101 and a subject information storage unit 2102. The image storage unit 2101 stores the subject's eye images 21. The subject information storage unit 2102 stores the subject information 23 including the identification information 24 of the subject. Typical examples of information included in the subject information 23 are the identification information 24, name, date of birth, gender, and the like. The code system of the identification information 24 may be different from that of the patient ID managed by the electronic medical record system 50.

The control unit 200 centrally controls each function of the ophthalmology imaging device 20. The control unit 200 is, for example, a processor such as a CPU. For example, the control unit 200 reads out a program for realizing each function from the storage unit 210 and expands the program to the RAM. The control unit 200 includes a mode switching unit 201, an operation control unit 202, a subject information receiving unit 203, and an association unit 205 as a result of the expansion.

The mode switching unit 201 switches the operation mode of the ophthalmology imaging device 20. Specifically, the mode switching unit 201 switches between the local mode and the remote mode. The mode switching unit 201 typically switches the mode according to an input operation received by the input unit 207. Alternatively, the mode switching unit 201 may switch the mode according to instructions from an external device. Further, the mode switching unit 201 may switch the mode according to a predetermined rule.

The operation control unit 202 controls the imaging unit 206 and executes the imaging-related operation. The operation control unit 202 switches between the remote mode and the local mode.

The processing contents of the operation control unit 202 in the remote mode are as follows. The operation control unit 202 executes the imaging-related operations according to instructions from the ophthalmology information processing system 1 (specifically, the ophthalmology information processing device 10). As such, the operation control unit 202 causes the imaging unit 206 to take the subject's eye image 21. If a command is transmitted from the ophthalmology information processing device 10 via the software IF 1013, the operation control unit 202 may receive the command. The operation control unit 202 may then execute the imaging-related operation according to the content of the received command. The operation control unit 202 acquires the subject's eye image 21 taken by the imaging unit 206. The operation control unit 202 may add related information to the acquired subject's eye image 21. The related information may be, for example, identification information of the imaging unit 206. The operation control unit 202 transmits the acquired eye image 21 to the ophthalmology information processing system 1 (specifically, the ophthalmology information processing device 10). Here, it should be noted that the subject's eye image 21 is not associated with the identification information of the subject. The transmitted subject's eye image 21 is acquired by the image acquisition unit 1012 via the software IF 1013 in the ophthalmology information processing device 10. Note that the operation control unit 202 may store the subject's eye image 21 in the image storage unit 2101. The subject's eye image 21 stored in the image storage unit 2101 may be output (displayed, printed, etc.) to an output device (not shown).

The processing contents of the operation control unit 202 in the local mode are as follows. The operation control unit 202 follows input operations from the input unit 207. Therefore, the operation control unit 202 causes the imaging unit 206 to take the subject's eye image 21 by executing the imaging-related operation. The operation control unit 202 acquires the subject's eye image 21 taken by the imaging unit 206. The operation control unit 202 may add related information to the acquired subject's eye image 21. The related information may be, for example, identification information of the imaging unit 206. The operation control unit 202 transmits the subject's eye image 21 taken by the imaging unit 206 to the association unit 205. The operation control unit 202 may acquire the subject's eye image 22 from the association unit 205. The subject's eye image 22 is generated by the association unit 205 based on the subject's eye image 21. Further, the subject's eye image 22 is associated with the patient information 23 including the identification information 24. The operation control unit 202 may transmit the acquired eye image 22 to the ophthalmology information processing system 1 (specifically, the ophthalmology information processing device 10). Note that the operation control unit 202 may store the subject's eye image 22 in the image storage unit 2101. the subject's eye image 22 stored in the image storage unit 2101 may be output (displayed, printed, etc.) to an output device (not shown).

The subject information receiving unit 203 accepts input or selection of the subject information 23 in accordance with an input operation from the input unit 207 during the local mode. The person performing the input operation may be the subject. Alternatively, the person performing the input operation may be a medical staff. The subject information 23 may be newly input. Alternatively, the subject information 23 may be read from the subject information storage unit 2102 and selected. The subject information 23 includes at least the identification information 24 of the subject. The identification information 24 may be newly issued. Alternatively, the identification information 24 may be read from the subject information storage unit 2102 and selected.

In the remote mode, the subject information receiving unit 203 may operate in the same manner as in the local mode. Alternatively, the subject information receiving unit 203 may not accept input or selection of the subject information 23. In the latter case, the subject information receiving unit 203 may display, on the input unit 207 which also has a display function, a message that the input or selection of the subject information 23 is not accepted. Alternatively, the subject information receiving unit 203 may cause a display unit (not shown) to display such a message.

In the remote mode, the operation control unit 202 may perform imaging-related operations regardless of whether the subject information 23 is input. That is, in the remote mode, even if the subject information receiving unit 203 receives the input or selection of the subject information 23, the operation control unit 202 may execute the imaging-related operation instructed under the remote mode.

Figure 8:
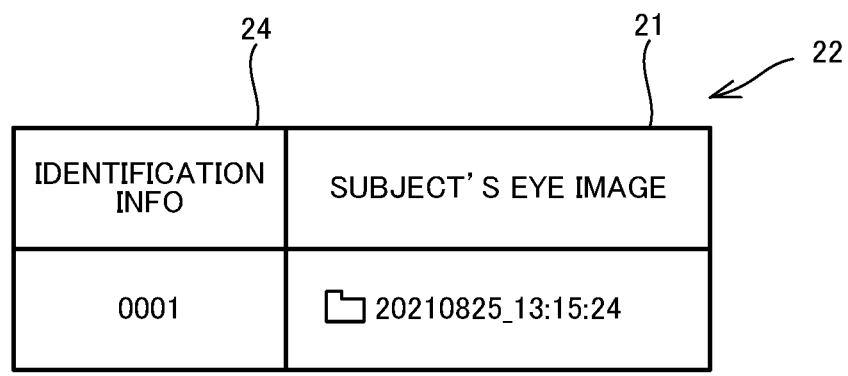
FIG. 8 is a diagram showing an example of a data structure of a subject's eye image with identification information.

The association unit 205 acquires the subject's eye image 21 taken by the imaging unit 206 from the operation control unit 202 during the local mode. The association unit 205 generates the subject's eye image 22 by associating the acquired subject's eye image 21 with the subject information 23 that includes at least the identification information 24 and is received by the subject information receiving unit 203. FIG. 8 is a diagram showing an example of the data structure of the subject's eye image 22 attached with the identification information. In the example shown in FIG. 8, the subject's eye image 21 is expressed as one folder. It should be understood that one or more files (not shown) related to the subject's eye image 21 are present in the folder. In the example shown in FIG. 8, only the identification information 24 is associated with the subject's eye image 21, which is not necessarily limited to this. For example, in addition to the identification information 24, the association unit 205 may associate the subject information 23 (such as name) other than the identification information 24 with the subject's eye image 21. That is, the association unit 205 may generate the subject's eye image 22.

The association unit 205 may operate in the remote mode in the same manner as in the local mode. Furthermore, the association unit 205 may stop operating.

The association unit 205 may store the subject's eye image 22 in the image storage unit 2101.

<Processing Flow>

Figure 9:
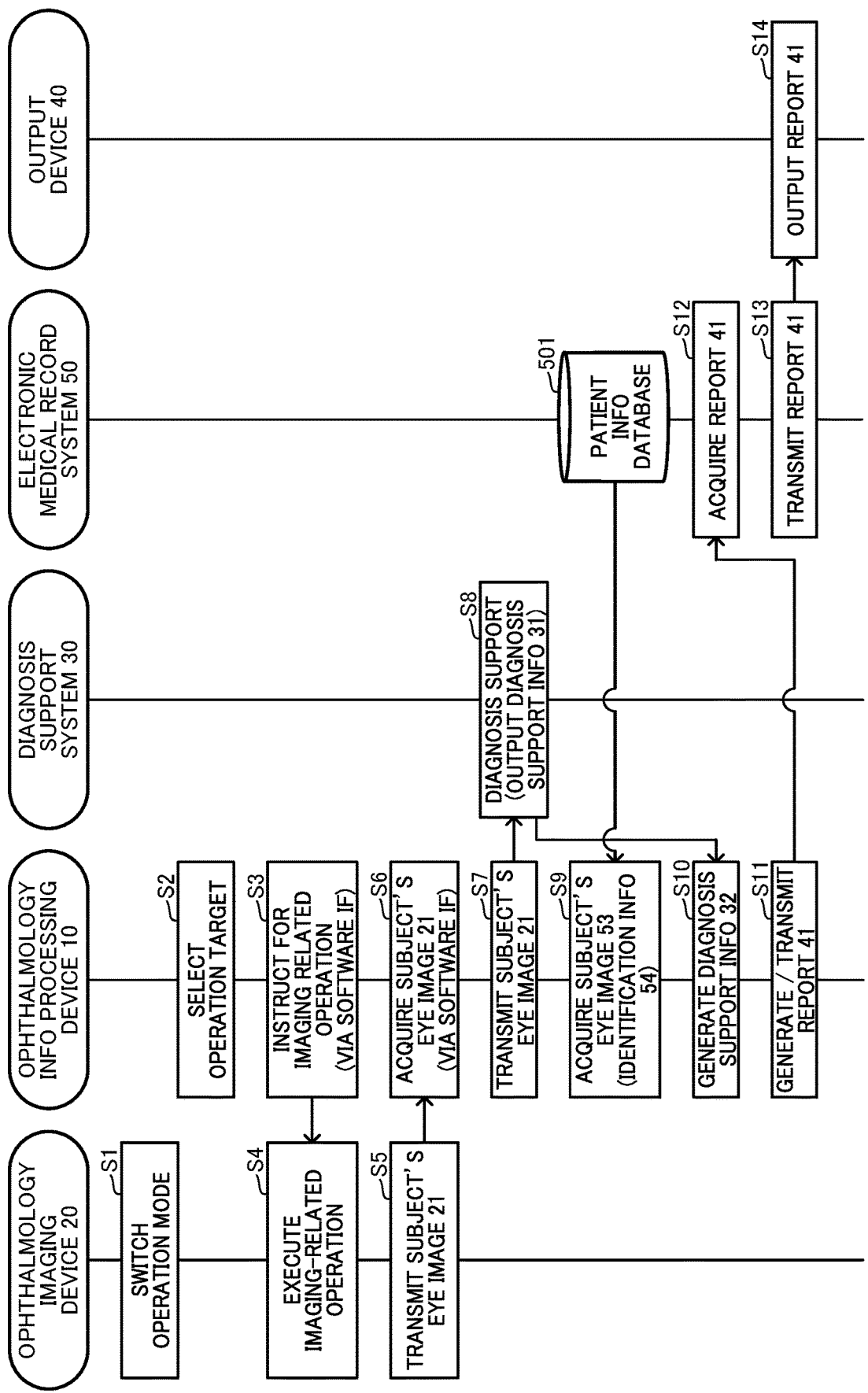
FIG. 9 is a sequence diagram showing an example of a flow of processing until a report is obtained based on a subject's eye image taken by the ophthalmology imaging device operating in a remote mode.

FIG. 9 is a sequence diagram showing an example of a flow of processing until the report 41 is obtained based on the subject's eye image 21 taken by the ophthalmology imaging device 20 operating in the remote mode. Each process in the ophthalmology information processing system 1 is executed and controlled by one or more information processing devices. At least one information processing device may be communicably connected to the ophthalmology imaging device 20.

In the ophthalmology imaging device 20, the mode switching unit 201 switches the mode to the remote mode in response to an input operation received by the input unit 207 (step S1). Note that step S1 may be executed at the latest before step S3 is executed.

In the ophthalmology information processing device 10, the operation target selection unit 103 selects the ophthalmology imaging device 20 that is a target for operation (step S2). The operation instruction unit 1011 instructs the ophthalmology imaging device 20 selected at step S2 to perform an imaging-related operation via the software IF 1013 (step S3, an instruction step).

In the ophthalmology imaging device 20, the operation control unit 202 executes the imaging-related operation instructed at step S3 (step S4). Thereby, the imaging unit 206 captures the subject's eye image 21. Then, the operation control unit 202 transmits the subject's eye image 21 to the ophthalmology information processing device 10 (step S5).

The processing in the ophthalmology information processing device 10 is as follows. The image acquisition unit 1012 acquires the subject's eye image 21 transmitted at step S5. More specifically, the image acquisition unit 1012 acquires the eye image 21 from the ophthalmology imaging device 20 via the software IF 1013 (step S6, an acquisition step). That is, the image acquisition unit 1012 acquires the subject's eye image 21 that is taken according to the instruction at step S3. The image acquisition unit 1012 transmits the subject's eye image 21 acquired at step S6 to the diagnosis support system 30 (step S7).

In the diagnosis support system 30, the diagnosis support unit 301 receives the subject's eye image 21 acquired at step S6 and transmitted at step S7. The diagnosis support unit 301 receives, as an input, the received subject's eye image 21 and outputs, as an output, the diagnosis support information 31 for the subject's eye image 21 (step S8, a diagnosis support step).

In the ophthalmology information processing device 10, the subject information acquisition unit 104 acquires, from the electronic medical record system 50, the subject information 53 on the subject whose eye image 21 was taken at step S6 (step S6). S9). Note that step S9 may be executed before step S7.

The association unit 105 associates the diagnosis support information 31 output at step S8 with the identification information 54 included in the subject information 53 acquired at step S9. Thereby, the association unit 105 generates the diagnosis support information 32 (step S10). The report generation unit 106 generates the report 41 including the diagnosis support information 32 generated at step S10. The report generation unit 106 transmits the generated report 41 to the electronic medical record system 50 (step S11).

The electronic medical record system 50 acquires the report 41 transmitted at step S11 (step S12). The electronic medical record system 50 transmits the acquired report 41 to the output device 40 (step S13). The output device 40 acquires the report 41 transmitted at step S13. The output device 40 outputs the acquired report 41 (step S14).

Through the above procedure, the ophthalmology information processing system 1 acquires the subject's eye image 21 taken by the ophthalmology imaging device 20 operating in the remote mode. The ophthalmology information processing system 1 outputs the diagnosis support information 31 regarding the subject's eye image 21 based on the acquired subject's eye image 21. Further, the ophthalmology information processing system 1 generates the report 41 including the diagnosis support information 32. The ophthalmology information processing system 1 transmits the generated report 41 to the electronic medical record system 50. Then, the electronic medical record system 50 transmits the report 41 to the output device 40. Thereby, the subject or a medical person who is the user of the output device 40 can view the report 41.

Further, the software IF 1013 is used for communication with the ophthalmology imaging device 20. Therefore, the ophthalmology information processing system provider can easily design and develop software required for interacting with the ophthalmology imaging device 20 at low cost. In addition, the ophthalmology information processing system provider can design and develop the specifications and software for the ophthalmology imaging device 20 with a high degree of freedom without subject to constraints such as the environment.

Furthermore, the ophthalmology information processing system 1 can generate the diagnosis support information 32 associated with the identification information 54 without depending on the ophthalmology imaging device 20. Therefore, it is not necessary to register and manage identification information of subjects in the ophthalmology imaging device 20. Furthermore, the identification information does not need to be linked between the ophthalmology imaging device 20 and the ophthalmology information processing system 1. For the reasons described above, using the ophthalmology information processing system 1, it is possible to reduce the complexity involved in registering and managing the identification information of subjects.

FIG. 10 is a sequence diagram showing an example of a flow of processing until the report 41 is obtained based on the subject's eye image 22 taken by the ophthalmology imaging device 20 operating in the local mode. Each process in the ophthalmology information processing system 1 is executed and controlled by one or more information processing devices. At least one information processing device may be communicably connected to the ophthalmology imaging device 20.

In the ophthalmology imaging device 20, the mode switching unit 201 switches the mode to the local mode in response to an input operation received by the input unit 207 (step S21). The operation control unit 202 executes the imaging-related operations according to the input operation from the input unit 207 (step S22). The subject information receiving unit 203 receives input or selection of the subject information 23 including at least the identification information 24 in accordance with the input operation from the input unit 207 (step S23). Step S23 may be executed before step S22. The association unit 205 generates the subject's eye image 21 taken by the imaging-related operation of the by the imaging unit 206 executed at step S22. Furthermore, the association unit 205 generates the subject's eye image 22 based on the subject information 23 received at step S23 (step S24). The operation control unit 202 transmits the subject's eye image 22 generated at step S24 to the ophthalmology information processing device 10 (step S25).

In the ophthalmology information processing device 10, the image acquisition unit 1012 acquires the subject's eye image 22 transmitted at step S25 via the software IF 1013 (step S26). The image acquisition unit 1012 transmits the subject's eye image 22 acquired at step S26 to the diagnosis support system 30 (step S27).

In the diagnosis support system 30, the diagnosis support unit 301 receives the subject's eye image 22 transmitted at step S27. The diagnosis support unit 301 inputs the received eye image 22. Then, the diagnosis support unit 301 outputs the diagnosis support information 33 for the subject's eye image 22 (step S28).

The report generation unit 106 generates the report 41 including the diagnosis support information 33 output at step S28. The report generation unit 106 transmits the generated report 41 to the electronic medical record system 50 (step S29).

The electronic medical record system 50 acquires the report 41 transmitted at step S29 (step S30). The electronic medical record system 50 transmits the acquired report 41 to the output device 40 (step S31). The output device 40 acquires the report 41 transmitted at step S31. Then, the output device 40 outputs the report 41 (step S32).

Through the above procedure, the ophthalmology information processing system 1 acquires the subject's eye image 22 taken by the ophthalmology imaging device 20 operating in the local mode. The ophthalmology information processing system 1 outputs the diagnosis support information 33 regarding the subject's eye image 22 based on the acquired subject's eye image 22. Further, the ophthalmology information processing system 1 generates the report 41 including the diagnosis support information 33. The ophthalmology information processing system 1 transmits the generated report 41 to the electronic medical record system 50. Then, the electronic medical record system 50 transmits the report 41 to the output device 40. Thereby, the subject or a medical person who is the user of the output device 40 can view the report 41.

In this way, the ophthalmology information processing system 1 can also generate the diagnosis support information 33 and the report 41 based on the subject's eye image 22 taken by the ophthalmology imaging device 20 operating in the local mode.

The ophthalmology information processing system 1 may be provided by the ophthalmology information processing system provider as a program for realizing each function of the ophthalmology information processing system 1. That is, the ophthalmology information processing system provider may provide a program for realizing each function of the operation instruction unit 1011 that executes the instruction step, the image acquisition unit 1012 that executes the acquisition step, and the diagnosis support unit 301 that executes the diagnosis support processing step. At the instruction step, instructions are generated in accordance with the specifications of the software IF 1013. At the instruction step, the instruction is given to the ophthalmology imaging device 20. The ophthalmology imaging device 20 executes the imaging-related operations based on the instruction. Therefore, each function realized by the program provided by the ophthalmology information processing system provider is used. As a result, a series of processes from taking the subject's eye image 21 by the ophthalmological photographing device 20 to obtaining the diagnosis support information 31 and 33 based on the subject's eye image 21 can be performed without being constrained. This restriction depends on other specifications of the ophthalmology imaging device 20 provided by the ophthalmology imaging device provider, the environment, and the like. Further, for the ophthalmology imaging device provider, there is no need to customize the ophthalmology imaging device 20 to meet the specifications of the ophthalmology information processing system 1 provided by the ophthalmology information processing system provider. Accordingly, the ophthalmology information processing system provider can efficiently operate the ophthalmology imaging device 20 based on instructions from the ophthalmology information processing system 1.

In the present disclosure, the term "processor" may refer to a single hardware processor or several hardware processors that are configured to execute computer program code (i.e., one or more instructions of a program) included in a program. In other words, a processor may be one or more programmable hardware devices. For instance, a processor may be a general-purpose or embedded processor and include, but not necessarily limited to, CPU (a Central Processing Circuit), a microprocessor, GPU (a Graphics Processing Unit), and DFP (a Data Flow Processor).

The term "memory" in the present disclosure is a non-transitory, tangible storage medium, and may refer to a single or several hardware memories configured to store computer program code (i.e., one or more instructions of a program) and/or data accessible by a processor. A memory may be implemented using any suitable memory technology, such as static random-access memory (SRAM), synchronous dynamic RAM (SDRAM), nonvolatile/Flash-type memory, or any other type of memory. Computer program code constituting a program may be stored on the memory and, when executed by a processor, cause the ophthalmology information processing system to perform the above-described various functions.

In the present disclosure, the term "circuit" may refer to a single hardware logical circuit or several hardware logical circuits (in other words, "circuitry") that are configured to cause the ophthalmology information processing system to perform one or more functions. In other words (and in contrast to the term "processor"), the term "circuit" refers to one or more non-programmable devices. For instance, a circuit may be a customized IC (an Integrated Circuit) that is customized for a particular use and is configured as non-programmable.

In the present disclosure, the phrase "at least one of (i) a circuit and (ii) a processor" should be understood as disjunctive (logical disjunction) where the circuit and the processor can be optional and not be construed to mean "at least one of a circuit and at least one of a processor". Therefore, in the present disclosure, the phrase "at least one of a circuit and a processor is configured to cause the ophthalmology information processing system to perform functions" should be understood as "only the circuit can cause the ophthalmology information processing system to perform all the functions". Further, the phrase "at least one of a circuit and a processor is configured to cause the ophthalmology information processing system to perform functions" should be understood as "only the processor can cause the ophthalmology information processing system to perform all the functions". Moreover, the phrase "at least one of a circuit and a processor is configured to cause the ophthalmology information processing system to perform functions" should be understood as "the circuit can cause the ophthalmology information processing system to perform at least one of the functions and the processor can cause the ophthalmology information processing system to perform the remaining functions". In the last example, if the ophthalmology information processing system performs functions A to C, for example, the functions A and B among the functions A to C may be implemented via a circuit, while the remaining function C may be implemented via a processor.

The present disclosure is not necessarily limited to the embodiments described above.

The invention claimed is:

1. A control method executed by an information processing device communicably connected to an ophthalmology imaging device including (i) an imaging unit that is configured to take a subject's eye image and (ii) an operation control unit that is configured to execute an imaging-related operation related to taking of the subject's eye image in accordance with an input operation directly input into the ophthalmology imaging device and is configured to execute the imaging-related operation in accordance with an instruction remotely transmitted, the method comprising:

an instruction step of transmitting the instruction to the ophthalmology imaging device as an operation target to execute the imaging-related operation;
an acquisition step of acquiring, from the ophthalmology imaging device, the subject's eye image that was taken in accordance with the instruction; and
a diagnosis support step of outputting diagnosis support information for the subject's eye image, wherein
the imaging-related operation includes at least one of starting of an imaging sequence, stopping of the imaging sequence, switching between a left subject's eye and a right subject's eye, optimization of the imaging unit, alignment, capture, an initial operation associated with switching of patients, and transition to an imaging standby state,
the instruction step further comprises generating the instruction to meet a specification of an API (Application Programming Interface) or an SDK (Software Development Kit) as a software interface,
the ophthalmology imaging device is provided by a first business provider,
a program for causing the information processing device to execute the instruction step, the acquisition step, and the diagnosis support step is provided by a second business provider that is different from the first business provider,
the instruction step further comprises generating the instruction to meet the specification of the API or the SDK that was provided by the first business provider to the second business provider, and
the operation control unit executes the imaging-related operation in accordance with the instruction.

2. The control method according to claim 1, wherein the imaging-related operation further includes transfer of imaging data.

3. A control method executed by an information processing device communicably connected to an ophthalmology imaging device including (i) an imaging unit that is configured to take a subject's eye image and (ii) an operation control unit that is configured to execute an imaging-related operation related to taking of the subject's eye image in accordance with an input operation directly input into the ophthalmology imaging device and is configured to execute the imaging-related operation in accordance with an instruction remotely transmitted, the method comprising:
an instruction step of transmitting the instruction to the ophthalmology imaging device as an operation target to execute the imaging-related operation;
an acquisition step of acquiring, from the ophthalmology imaging device, the subject's eye image that was taken in accordance with the instruction; and
a diagnosis support step of outputting diagnosis support information for the subject's eye image, wherein
the imaging-related operation includes at least one of starting of an imaging sequence, stopping of the imaging sequence, switching between a left subject's eye and a right subject's eye, optimization of the imaging unit, alignment, capture, an initial operation associated with switching of patients, and transition to an imaging standby state,
the instruction step further comprises generating the instruction to meet a specification of an API (Application Programming Interface) or an SDK (Software Development Kit) as a software interface,
the ophthalmology imaging device includes a mode switching unit that is configured to switch an operation mode of the ophthalmology imaging device between a local mode and a remote mode,
the operation control unit executes the imaging-related operation in accordance with the input operation directly input into the ophthalmology imaging device unit during the local mode, and
the operation control unit executes the imaging-related operation in accordance with the instruction remotely transmitted from the information processing device during the remote mode
the ophthalmology imaging device comprises:
a subject information receiving unit that is configured to receive identification information of a subject during the local mode; and
an association unit that is configured to associate the subject's eye image taken by the ophthalmology imaging device with the identification information received by the subject information receiving unit, and
the operation control unit is configured to:
transmit the subject's eye image being associated with the identification information to the information processing device during the local mode; and
transmit the subject's eye image not being associated with the identification information to the information processing device during the remote mode.

4. The control method according to claim 3, wherein when the ophthalmology imaging device is in the remote mode, the operation control unit is configured to execute the imaging-related operation regardless of whether the identification information is received.

5. An ophthalmology information processing system communicably connected to an ophthalmology imaging device including (i) an imaging unit that is configured to take a subject's eye image and (ii) an operation control unit that is configured to execute an imaging-related operation related to taking of the subject's eye image in accordance with an input operation directly input into the ophthalmology imaging device and is configured to execute the imaging-related operation in accordance with an instruction remotely transmitted, the system comprising:
at least one of (i) a circuit and (ii) a processor having a memory storing computer program code, wherein the at least one of the circuit and the processor is configured to cause the ophthalmology information processing system to:
transmit the instruction to the ophthalmology imaging device as an operation target to execute the imaging-related operation;
acquire, from the ophthalmology imaging device, the subject's eye image that was taken in accordance with the instruction; and
output diagnosis support information for the subject's eye image, wherein
the imaging-related operation includes at least one of starting of an imaging sequence, stopping of the imaging sequence, switching between a left subject's eye and a right subject's eye, optimization of the imaging unit, alignment, capture, an initial operation associated with switching of patients, and transition to an imaging standby state,
the at least one of the circuit and the processor is further configured to cause the ophthalmology information processing system to generate the instruction to meet a specification of an API (Application Programming Interface) or an SDK (Software Development Kit) as a software interface, the ophthalmology imaging device is provided by a first business provider, a program including the computer program code for the ophthalmology information processing system is provided by a second business provider that is different from the first business provider, the at least one of the circuit and the processor is further configured to cause the ophthalmology information processing system to generate the instruction to meet the specification of the API or the SDK that was provided by the first business provider to the second business provider, and the operation control unit of the ophthalmology imaging device executes the imaging-related operation in accordance with the instruction.

6. The control method according to claim 3, wherein the imaging-related operation further includes transfer of imaging data.

* * * * *